United States Patent [19]
Thompson

[11] Patent Number: 5,562,653
[45] Date of Patent: Oct. 8, 1996

[54] MEDICAL DEVICES COMPOSED OF LOW CEILING TEMPERATURE POLYMERS

[75] Inventor: Samuel A. Thompson, Wilmington, Del.

[73] Assignee: Hercules Incorporated, Wilmington, Del.

[21] Appl. No.: 340,564

[22] Filed: Nov. 16, 1994

[51] Int. Cl.⁶ .................................................. A61K 9/22
[52] U.S. Cl. ...................... 604/890.1; 604/265; 424/428
[58] Field of Search .................. 128/898; 604/890.1, 604/265; 424/422–426, 428

[56] References Cited

U.S. PATENT DOCUMENTS

| | | | |
|---|---|---|---|
| 4,108,839 | 8/1978 | Chambers et al. | 528/270 |
| 4,150,989 | 4/1979 | Chambers et al. | 96/35.1 |
| 4,409,206 | 10/1983 | Stricker | 602/51 |
| 4,595,713 | 6/1986 | St. John | 523/103 |
| 4,614,768 | 9/1986 | Lo | 525/250 |
| 4,650,488 | 3/1987 | Bays et al. | 623/12 |
| 4,738,257 | 4/1988 | Meyer et al. | 602/52 |
| 4,876,172 | 10/1989 | Hillenbrand | 430/253 |
| 4,911,926 | 3/1990 | Henry et al. | 424/426 |
| 4,925,677 | 5/1990 | Feijen | 424/484 |
| 5,085,629 | 2/1992 | Goldberg et al. | 604/8 |
| 5,126,141 | 6/1992 | Henry | 424/423 |
| 5,137,728 | 8/1992 | Bawa | 424/427 |
| 5,225,314 | 7/1993 | Waterman, et al. | 430/253 |
| 5,250,066 | 10/1993 | Lambert | 606/181 |
| 5,264,281 | 11/1993 | Arakawa et al. | 428/354 |
| 5,295,978 | 3/1994 | Fan et al. | 604/265 |
| 5,438,988 | 8/1995 | Duan et al. | 128/640 |

OTHER PUBLICATIONS

"Polymer Handbook, 2nd Edition", J. Wiley & Sons, NY, 1989, pp. II 421–II 450.

*Primary Examiner*—Randall L. Green
*Assistant Examiner*—Chalin Smith
*Attorney, Agent, or Firm*—Martin F. Sloan; Mark Goldberg

[57] ABSTRACT

The present invention provides shaped medical devices adapted for implant and subsequent in-vivo disintegration within a human or animal body. In one embodiment, the medical device is fabricated from a matrix polymer component, e.g., a lactam, which has a ceiling temperature (Tc) within the range of from about 40° C. to about 76° C. Decomposition of this device is accomplished by heating the device in-vivo to a temperature at or above the ceiling temperature of the matrix polymer component. In another embodiment, the medical device is fabricated from an end-capped polyoxyalkylene matrix polymer component characterized by a depolymerization temperature of at least about 40° C. and a ceiling temperature of 76° C. or less after removal of the end-cap group. In a third embodiment of the invention the medical device comprises a matrix polymer which is insoluble or only slightly soluble in normal body fluids and which exhibits a Tc below 40° C. This device is stored and handled at T<Tc such that depolymerization and disintegration of the device does not begin until the device is implanted.

27 Claims, No Drawings

MEDICAL DEVICES COMPOSED OF LOW CEILING TEMPERATURE POLYMERS

FIELD OF THE INVENTION

The invention relates to medical devices, e.g., implants composed of low ceiling temperature polymers which can be disintegrated in vivo upon demand by depolymerization of the polymer.

DESCRIPTION OF RELATED ART

Medical devices are often used to facilitate the flow of material as, for example, in a ureteral stent used for drainage of urine from the kidney to the bladder, or in a vascular graft used to maintain blood flow.

Typically these medical devices have been made from durable, non-biodegradable materials such as metals, polyurethanes, polyacrylates, silicones etc. These non-biodegradable, non-dissolvable medical devices typically must be removed via an invasive procedure after they have served their purpose, or they remain in the body indefinitely. For those devices which remain in-vivo, there are often medical complications such as inflammation and other foreign body responses.

Devices have also more recently been prepared from biodegradable materials such as polyesters, polyanhydrides, and polyorthoesters. In U.S. Pat. No. 5,085,629, the use of a biodegradable polyester terpolymer of lactide, glycolide, and epsilon-caprolactone in a ureteral stent is disclosed. In the '629 patent, biodegradable has been defined to include hydrolytic instability. These polymers undergo hydrolytic chain cleavage in the presence of water to form low molecular weight water soluble species. The polyesters have been reported to undergo hydrolysis throughout the thickness of the device simultaneously (homogeneous hydrolysis) while the polyanhydrides and polyorthoesters have been reported to hydrolyse from the surface (heterogeneous hydrolysis).

There are several problems inherent to devices manufactured with these biodegradable materials. There is a significant loss of strength in the device prior to any significant weight loss. These devices may undergo failure into large pieces which may occlude the vessel in which they have been deployed. Biodegradable devices which undergo surface hydrolysis may eventually reach a thin skin configuration that may also lead to vessel occlusion. Semicrystalline biodegradable materials have also been shown to leave insoluble crystalline residuals in the body for very long periods of time.

Polyoxyalkylene polymers have also been used in the formulation of various compositions for medical implants. For example, U.S. Pat. No. 4,595,713 discloses a biodegradable medical implant useful in the regeneration of soft and hard connective tissue, such as cartilage and bone, which comprises a copolymer of a major amount of epsilon caprolactone and a minor amount of lactide. Where regeneration of bone tissue, in particular, is desired, the copolymer may further include osteogenic material in powdered or particulate form.

In addition, U.S. Pat. Nos. 4,911,926 and 5,126,141 disclose processes and compositions for reducing post-surgical adhesion formation/reformation in mammals following injury to organs situated in mammalian body spaces. Aqueous, thermally reversible gel compositions, preferably at mammalian body fluid pH, comprising a polyoxyalkylene polymer and an ionic polysaccharide are applied to injured areas of the organs situated in body cavities such as, the peritoneal, pelvic, or pleural cavity. The aqueous compositions are gelled with a counter-ion.

A primary object of this invention is to provide temporary medical devices such as implants which are essentially insoluble in and relatively inert with respect to normal body fluids, but which can be quickly disintegrated in-vivo by a chemical or thermal trigger mechanism controlled by the physician.

SUMMARY OF THE INVENTION

The present invention provides shaped medical devices adapted for implant and subsequent in-vivo disintegration within a human or animal body. In one embodiment, the medical device is fabricated from a matrix polymer component, e.g., a lactam, which has a ceiling temperature (Tc) within the range of from about 40° C. to about 76° C. Decomposition of this device is accomplished by heating the device in-vivo to a temperature at or above the ceiling temperature of the matrix polymer component sufficient to depolymerize the matrix polymer thereby converting it to water soluble or water dispersible monomeric constituents which can be removed by flushing or by normal body processes.

In another embodiment, the medical device is fabricated from an end-capped matrix polymer component, e.g., an ester end-capped polyoxyalkylene polymer component, characterized by a depolymerization temperature of at least about 40° C., and a ceiling temperature of 76° C. or less after removal of the end-cap group. Decomposition of this device is accomplished by contacting the device in-vivo with a chemical releasing agent capable of displacing the end cap group and, optionally, the further application of heat, such that the polyoxyalkylene matrix polymer is converted to water soluble or water dispersible monomeric constituents which can be removed by flushing or by normal body processes.

In a third embodiment of the invention the medical device comprises a matrix polymer which is insoluble or only slightly soluble in normal body fluids and which exhibits a Tc below 40° C. This device is stored and handled at T<Tc such that depolymerization and disintegration of the device does not begin until the device is implanted, at which time the polymer will begin to depolymerize, and eventually the device disintegrates. In this embodiment the device has a set lifetime in the body which would be dictated by the Tc of the polymer composition, the temperature of the environment surrounding the device, and the rate of depolymerization. In this embodiment a trigger is not required to initiate the disintegration process.

The invention thus provides for temporary shaped medical device implants which can be easily removed from the body in-vivo and on demand by heat and/or by contact with a chemical agent which initiates decomposition of the implant, thereby eliminating the need for invasive surgical procedures to remove the device.

DETAILED DESCRIPTION OF THE INVENTION

The ceiling temperature (Tc) of a polymer may be defined as the temperature at which the free energy of polymerization ($\Delta F$) is equal to zero ($\Delta F = \Delta H - T\Delta S = 0$), i.e., $Tc = \Delta H/\Delta S$ where $\Delta H$ equals the enthalpy of polymerization and $\Delta S$ equals the entropy of polymerization.

For most chain polymerizations, there is some temperature (Tc) above which the rate of the polymerization reaction is exceeded by the rate of the depolymerization reaction. Below Tc, polymerization will propagate but as the reaction temperature increases, there is reached a point Tc where the propagation rate constant equals the depropagation rate constant. Above Tc, depolymerization is thermally favored, the polymer becomes unstable and depolymerizes into its monomeric constituents.

The present invention takes advantage of Tc phenomena by the utilization of polymeric matrix materials for the production of medical devices, e.g., implants, which are heat stable at temperatures of 40° C. or higher (higher than normal body temperature) in their stable state but which can be destabilized by the in-vivo application of heat or contact of the device with a chemical agent such that the polymeric material depolymerizes within the body, thereby disintegrating the medical device.

In one embodiment of the invention, the medical device comprises a matrix polymer material which is insoluble or only very slightly soluble in normal body fluids and which exhibits a Tc in the range of 40° C. to 76° C. Heating the device in-vivo by methods hereafter disclosed to a temperature above the Tc value for the particular polymer but not in excess of about 76° C. will cause the matrix polymer to disintegrate (depolymerize) into its monomeric constituents which are either water soluble or water dispersible. These monomeric constituents are then removed from the body by normal body processes or by flushing with aqueous saline solutions. The upper Tc limit of 76° C. is dictated primarily by the fact that this is the approximate limit to which physiological body fluids, e.g., blood, can be locally heated without gross delocalized cellular damage.

In a second embodiment of the invention, the medical device comprises an end-capped matrix polymer, e.g., an end-capped polyoxyalkylene (polyaldehyde) matrix polymer material which is also insoluble or only very slightly soluble in normal body fluids and which, in the stabilized end capped state, exhibits a depolymerization temperature of at least 40° C., e.g., 40°–250° C., but a Tc of 76° C. or less after in-vivo removal of the end cap groups. The term "depolymerization temperature" as used herein refers to the temperature at below which the end-capped polymer remains stable and does not depolymerize. In-vivo contact of the device with a chemical releasing agent capable of cleaving or splitting off the end cap group will destabilize an appropriately selected polymer matrix material such that the Tc of the resulting destabilized polymer will be lowered to 76° C. or below. Where the Tc of the resulting destabilized polymer lies in the range of 40° C. to 76° C., heat may be applied as described above to depolymerize the polymer into its monomeric constituents. Where the Tc of the resulting destabilized polymer is significantly below about 40° C., i.e., where the Tc is below normal body temperature, the medical device will disintegrate in-vivo without the application of additional heat as a consequence of the removal of the stabilizing end cap group.

Polymers having Tc characteristics as described herein are well known materials, but their use in the fabrication of medical devices has not heretofore been disclosed. A more complete description of ceiling temperature phenomenon and Tc values for various polymeric material may be found in the *Polymer Handbook*, 2nd edition, J. Wiley & Sons, NY, Editors J. Brandrup, et al., 1989, pages II 421–II 447, the complete disclosure of which is incorporated herein by reference.

In a third embodiment of the invention the medical device comprises a matrix polymer which is insoluble or only slightly soluble in normal body fluids and which exhibits a Tc below 40° C. This device is stored and handled at T<Tc such that depolymerization and disintegration of the device does not begin until the device is implanted, at which time the polymer begins to depolymerize, and eventually the device disintegrates. In this embodiment the device has a set lifetime in the body which is dictated by the Tc of the polymer composition, the temperature of the environment surrounding the device, and the rate of depolymerization. In this embodiment a trigger is not required to initiate the disintegration process.

Suitable polymers having a Tc within the range of 40° to 76° C. include but are not limited to the polymerization product of $C_3$–$C_5$ lactams such as poly-delta-valerolactam (Tc=60° C.) which is the polymerization product of 2-piperidone monomer; poly-gamma-butrolactam (Tc= 76° C.) which is the polymerization product of 2-pyrrolidone monomer. Other suitable polymers include poly-alpha-methylstyrene (Tc=54°–61° C.) and polyoxepane (Tc=41.5° C.). Copolymers having a Tc within the range of 40 to 76° C. include 1:1 molar copolymers of sulfur dioxide with an olefinically unsaturated comonomer having 2 to 6 carbon atoms. Preferred comonomers are selected from the group consisting of allyl acetate (Tc=45° C.), allyl alcohol (Tc=76° C.), allyl ethyl ether (Tc=68° C.), allyl formate (Tc= 45° C.), 1-butene (Tc= 64° C.), 2-butene (Tc= 38°–46° C.), 1-hexadecene (Tc= 69° C.), 1-hexene (Tc= 60° C.), 1-pentene (Tc= 63° C.), 4-penetenoic acid (Tc=66° C.), and mixtures thereof. Polymers other than the lactams are, however, less preferred for those implant applications where the depolymerization products will remain in the body, i.e., are not immediately flushed away, because the depolymerization products are more highly toxic.

Suitable heat stabilized end capped polymers which have a Tc of 76° C. or less after the end cap is removed include ester capped polyoxyalkylene polymers and copolymers, e.g., polymers and copolymers of $C_2$ to $C_5$ aldehydes such as n-valeraldehyde, acetaldehyde, n-propionaldehyde, butyraldehyde, isobutyraldehyde as well as halogenated derivatives thereof such as mono-, di- or tri-chloroacetaldehyde (chloral). These aldehyde polymers all exhibit Tc's of 18° C. or less after end cap removal, e.g., polytrichloroacetaldehyde Tc= 18° C., poly-n-valeraldehyde Tc= –42° C., polyacetaldehyde Tc= –31° C. and polypropionaldehyde Tc=–31° C.

The most preferred polymers for use in the present invention are poly-delta-valerolactam and poly-n-propionaldehyde which is end-capped through an ester linkage with an anhydride, e.g., acetic anhydride. Quite obviously, polymers whose depolymerization product yield monomers exhibiting serious toxicity problems are to be avoided.

Suitable polymers having Tc<40° C. include polyoxyalkylene polymers and copolymers, e.g., polymers and copolymers of $C_2$ to $C_5$ aldehydes such as n-valeraldehyde, acetaldehyde, n-propionaldehyde, butyraldehyde, isobutyraldehyde as well as halogenated derivatives thereof such as mono-, di- or tri- chloroacetaldehyde (chloral). These aldehyde polymers all exhibit Tc's of 18° C. or less, e.g., polytrichloroacetaldehyde Tc= 18° C., poly-n-valeraldehyde Tc=–42° C., polyacetaldehyde Tc=–31° C. and polypropionaldehyde Tc=–31° C.

The polymers of the present invention may be prepared by conventional gaseous, bulk or solution polymerization processes using conventional anionic or cationic polymerization catalysts. Suitable anionic catalysts include bases such as primary, secondary, or tertiary amines; metal alkyls, alkoxides, phenolates and carboxylates; hydrated alumina; phosphines and pyridine. Suitable cationic catalysts include Lewis acids of the metal halide type and protonic acids such as hydrochloric and acetic acids. Addition polymers may be prepared using conventional free radical or redox catalyst systems. Polymerization should be conducted at temperatures and pressures such that the temperature is maintained below the ceiling temperature of the desired polymerization product, since otherwise substantial polymerization will not take place.

Polyoxyalkylene polymers obtained by chain polymerization of carbonyl monomers are generally unstable at ambient temperatures (25° C.) due to ceiling temperature effects. These polymers may be stabilized by converting their reactive hydroxyl end groups into unreactive ester linkages by an esterification or chain transfer reaction with an organic acid, acid halide or anhydride. A preferred technique is to include stoichiometric quantities of a mono- or polyfunctional acid anhydride such as acetic, proprionic or maleic anhydride in the polymerization recipe during or towards the termination of polymerization to provide stable RCOO—end groups. Where a polyfunctional anhydride is used, such as maleic anhydride, the end cap groups would be polymer end caps, e.g., stable RCOOR type end groups, which could also be characterized as internal groups linking two or more polymer chain segments. Thus, uncapped polyoxyalkylene polymers having Tc values less than body temperature are transformed into stable, end capped polymers having a depolymerization temperature in excess of 40° C. up to about 250° C.

Polymers useful as matrix polymer components in the medical devices of this invention generally have a number average molecular weight in the range of from about 5,000 to about 10,000,000; more preferably from about 10,000 to about 1,000,000.

Shaped medical devices prepared from the composition of this invention may take any form, for example, films, rods, cylindrical tubing or stents. Methods of fabrication include any of the standard polymer shaping methods known in the art, care being taken to avoid exposure to high temperatures which approach the Tc of the polymer and to avoid contact of the polymer with agents which may act to remove end caps where the polymer is end capped. Preferred methods of shaping include solvent casting, precipitation casting, low temperature machining and molding. Molding techniques include bulk polymerization of the polymer in a mold which has the shape of the desired device, e.g., a cylindrical mold having a core pin to produce hollow stents, or low temperature injection or extrusion molding, or reaction injection molding of monomers.

The shaped medical device may be disintegrated in-vivo by subjecting it to heat sufficient to raise the temperature of the device above the Tc of the matrix polymeric component, by physical contact of the device with a chemical releasing agent capable of displacing polymer end cap groups or by a combination of these methods.

Various heat sources which may be used to heat the device in-vivo include laser, infrared, and ultraviolet heat sources, Rf, microwave, ultrasound stimulation, and contact of the device with a balloon catheter containing a hot saline solution.

Chemical agents which are capable of removing end caps where the matrix polymer is end-capped include acids, bases, nucleophiles and enzymes. The most preferred agents are esterases. Methods for contact of the agent with the device include introduction through the diet of the patient, through parenteral feed, introduction of a solution directly onto the device such as by insertion of a catheter which injects the agent within the device, or through an enema. The medical devices are thereby removed as a consequence of the displacement of the stabilizing end cap groups present in the matrix polymer which has the effect of lowering polymer Tc. The disintegrated device is thereby removed safely from the body in the form of water soluble or water dispersible components. Where the Tc of the destabilized polymer remains above body temperature, a heating step as described above will be necessary to depolymerize the destabilized polymer.

Medical devices which may be fabricated in accordance with this invention include stents, catheter or cannula components, plugs and constrictors, for both human and animal use. The invention is particularly applicable to medical stents of tubular configuration which come in contact with one or more body fluids such as blood, urine, gastrointestinal fluids, and bile. The devices are particularly applicable for use in gastrointestinal, urogenital, cardiovascular, lymphatic, otorhinolaryngological, optical, neurological, integument and muscular body systems.

The devices may optionally include water, fillers, other additives for medical treatment such as antiseptics, antibiotics, anticoagulants, or medicines, and additives for mechanical property adjustment of the device.

The medical devices of this invention are useful in medical applications where the removal of the standard non-disintegratable medical device involves patient discomfort and/or expense and in applications where a temporary device is therapeutically desirable. Examples of useful applications for these devices include ureteral, urethral, bilial, ileal and pyloric stents. In these applications, current state of the art stents must be removed by a second invasive procedure at great expense and patient discomfort. The devices of this invention facilitate removal, leading to reduced patient discomfort and expense. The medical devices of this invention are also useful in cardiovascular, lymphatic, neurological, integumental, skeletal, muscular, optical, otorhinolaryngological, oral, gastrointestinal and urogenital applications where controlled disintegration of the device is efficacious and in surgical procedures where a device is needed temporarily such as a cellular scaffold after which removal by dissolution is preferred. Other medical device applications may include adhesion prevention devices, drainage devices as in ear or sinus tubes, release devices in dental and medical applications, wound care as in the treatment of bed sores, temporary scaffold for bone, osteophilic coatings, neural growth guides, temporary stent for anastomosis, shaped delivery devices, hemostats, surgical sponges, hydrocephalus shunt, dialysis tubing, instrument coatings, patches for delivery systems, ostomy bags, temporary plug, artificial skin, dental socket filler having therapeutic additives, temporary vena cava filter device, capsule for delivery of vena cava filter devices, deep vein thrombosis filter for orthopedic applications, dissolvable enteral feeding tube, internal plugs, and hiatal hernia stents. Any of these devices may also act to release medicines, nutrients and the like.

One preferred area of utility for the medical devices of this invention is an alternative treatment for benign prostatic hypertrophy (BPH). One serious problem with existing metal stents used in the treatment of BPH is that they do not allow for a secondary trans urethral resectioning of the prostate (TURP) procedure when prostrate tissue ingrowth through the metal coil begins to occlude the urethra. The metal stents currently used are difficult to remove without serious patient trauma. The medical devices of this invention can be removed from the body by removing the polymer endcap or simply by heating above the Tc. Monomers released upon depolymerization can be flushed from the urethra.

What is claimed is:

1. A shaped medical implant comprising a component comprised of matrix polymer having a ceiling temperature within the range of from about 40° to about 76° C., said implant being adapted for in-vivo disintegration by depolymerization within a human or animal body.

2. The implant of claim 1 wherein said matrix polymer is selected from the group consisting of polymers formed by polymerization of lactams having from 3 to 5 carbon atoms, poly-alpha-methylstyrene, polyoxepane and 1:1 molar copolymers of sulfur dioxide with an olefinically unsaturated monomer.

3. The implant of claim 2 wherein said matrix polymer is formed by polymerization of a lactam having from 3 to 5 carbon atoms.

4. The implant of claim 3 wherein said matrix polymer is poly-delta-valerolactam.

5. A shaped medical implant comprising a component comprised of either matrix polymer end-capped with an end cap group or matrix copolymer end-capped with an end cap group, said end-capped polymer or end-capped copolymer further characterized by a depolymerization temperature of at least 40° C., and a ceiling temperature of 76° C. or less after removal of said end cap group, and said implant being adopted for in-vivo disintegration by depolymerization within a human or animal body.

6. The implant of claim 5 wherein said matrix polymer is a polyoxyalkylene polymer.

7. The implant of claim 6 wherein said polyoxyalkylene polymer is a polymer or copolymer of a $C_2$ to $C_5$ aldehyde.

8. The implant of claim 7 wherein said end cap group is an ester linked to said aldehyde polymer.

9. The implant of claim 7 wherein said polymer of an aldehyde is selected from the group consisting of poly-acetaldehyde, poly-n-propionaldehyde, poly-butyraldehyde, poly-isobutyraldehyde, poly-n-valeraldehyde and halogenated derivatives thereof.

10. The implant of claim 9 wherein said polymer of an aldehyde is poly-n-propionaldehyde.

11. The implant of claim 10 wherein said end cap group is acetate ester.

12. The implant of claim 5 wherein said polymer is characterized by a ceiling temperature of 18° C. or less after removal of said end cap group.

13. A process for the in-vivo disintegration of the medical implant of claim 1 implanted in a human or animal body comprising heating said device in-vivo to a temperature at or above the ceiling temperature of said matrix polymer and sufficient to depolymerize said matrix polymer.

14. The process of claim 13 wherein said matrix polymer is selected from the group consisting of the polymerization product of $C_3$–$C_5$ lactams, poly-alpha-methylstyrene, polyoxepane and 1:1 molar copolymers of sulfur dioxide with an olefinically unsaturated monomer.

15. The process of claim 14 wherein said matrix polymer is the polymerization product of a $C_3$–$C_5$ lactam.

16. The process of claim 15 wherein said matrix polymer is poly-delta-valerolactam.

17. A process for the in-vivo disintegration of the medical implant of claim 5 implanted in a human or animal body comprising contacting said implant in-vivo with a releasing agent capable of displacing said end-cap group.

18. The process of claim 17 wherein said matrix polymer is a polyoxyalkylene polymer.

19. The process of claim 18 wherein said polyoxylalkylene polymer is a polymer or copolymer of a $C_2$ to $C_5$ aldehyde.

20. The process of claim 19 wherein said releasing agent is selected from the group consisting of acids, bases, nucleophiles and enzymes.

21. The process of claim 19 wherein said end cap group is an ester and said releasing agent is an esterase.

22. The process of claim 19 wherein said polymer of an aldehyde is poly-n-propionaldehyde.

23. The process of claim 22 wherein said end cap group is acetate ester.

24. The process of claim 17 wherein, after contact with said releasing agent, said implant is then heated to a temperature at or above the ceiling temperature of said polymer.

25. A shaped medical implant comprising a component comprised of matrix polymer having a ceiling temperature below 40° C., said implant being adapted for in-vivo disintegration by depolymerization within a human or animal body.

26. The medical implant of claim 25 wherein said matrix polymer is a polyoxyalkylene polymer.

27. The medical implant of claim 26 wherein said polyoxylalkylene polymer is a polymer or copolymer of a $C_2$ to $C_5$ aldehyde.

* * * * *

UNITED STATES PATENT AND TRADEMARK OFFICE
CERTIFICATE OF CORRECTION

PATENT NO. : 5,562,653

DATED : October 8, 1996

INVENTOR(S) : Samuel A. Thompson

It is certified that error appears in the above-identified patent and that said Letters Patent is hereby corrected as shown below:

In column 7, line 30, delete "adopted" and replace it with --adapted--.

Signed and Sealed this

Twenty-fourth Day of December, 1996

*Attest:*

BRUCE LEHMAN

*Attesting Officer*      *Commissioner of Patents and Trademarks*